United States Patent [19]

Taylor

[11] Patent Number: 5,695,552
[45] Date of Patent: Dec. 9, 1997

[54] AQUATIC ANTIFOULING COMPOSITIONS AND METHODS

[75] Inventor: Gordon T. Taylor, East Setauket, N.Y.

[73] Assignee: Research Foundation of State University of New York, Stonybrook, N.Y.

[21] Appl. No.: 799,290

[22] Filed: Feb. 13, 1997

Related U.S. Application Data

[63] Continuation of Ser. No. 164,328, Dec. 9, 1993, abandoned.

[51] Int. Cl.[6] .......................... A01N 63/00; A01N 25/00
[52] U.S. Cl. .................. 106/15.05; 422/6; 424/78.09; 424/93.7; 424/520; 424/538; 424/547; 427/384; 427/385.5; 427/393; 427/393.6; 427/397; 523/122; 523/177
[58] Field of Search ..................... 106/15.05; 422/6; 424/78.09, 93.7, 520, 538, 547; 427/384, 385.5, 393, 393.6, 397; 514/918; 523/122, 177

[56] References Cited

U.S. PATENT DOCUMENTS

| | | | |
|---|---|---|---|
| 2,138,831 | 12/1938 | Brammer | 422/6 |
| 3,415,928 | 12/1968 | Nadal et al. | 424/195.1 |
| 3,441,439 | 4/1969 | Eagell | 134/37 |
| 4,259,269 | 3/1981 | Flowers | 261/151 |
| 4,313,827 | 2/1982 | Ratigan et al. | 210/136 |
| 4,328,638 | 5/1982 | Smithson | 424/708 |
| 4,556,486 | 12/1985 | Merket | 210/170 |
| 4,788,302 | 11/1988 | Costlow et al. | 106/15.05 |
| 4,818,413 | 4/1989 | Hoover et al. | 210/739 |
| 4,857,209 | 8/1989 | Lyons et al. | 210/755 |
| 5,008,075 | 4/1991 | Rufolo | 422/6 |
| 5,096,488 | 3/1992 | Stovicek | 106/18.32 |
| 5,116,407 | 5/1992 | Hunter et al. | 106/16 |
| 5,143,545 | 9/1992 | Stiffey et al. | 106/15.05 |
| 5,199,977 | 4/1993 | Yamamori et al. | 106/15.05 |

FOREIGN PATENT DOCUMENTS

| | | |
|---|---|---|
| 0556949 | 8/1993 | European Pat. Off. |
| 0593135 | 4/1994 | European Pat. Off. |
| 4252284 | 9/1992 | Japan |
| 5-4903 | 5/1993 | Japan |
| 5155873 | 6/1993 | Japan |
| 5271009 | 10/1993 | Japan |
| 2 159 056 A | 11/1995 | United Kingdom |
| 8901512 | 2/1989 | WIPO |

OTHER PUBLICATIONS

Dilip de Silva et al., Three New Sesterterpenoid Antibiotics From the Marine Sponge *Luffariella variablis*, Tetrahedon Letters, vol., 22, No. 33, pp. 3147–3150 (1981) no month.

Nakatsu et al., Antimicrobial Constituents of *Udotea flabellum*, The Journal of Organic Chemistry, vol. 46, No. 12, pp, 2435–2438 (1981) no month.

Lindquist et al., Isolation and Structure Determination of Diazonmaides A and B, Unusual Cytotoxic Metabolites from the Marine Ascidian *Diazona chinensis*, J. Am. Chem. Soc, 113, pp. 2303–2304, (1991) no month.

Keifer et al., Renillafoulins, Antifouling Dieterpenes from the Sea Pansy Renilla, J. Org. Chem., 51 pp. 4450–4454 (1986) no month.

Teeyapant et al., Antibiotic and Cytotoxic Activity of Brominated Compounds from the Marine Sponge *Verongia aerophoba*, J. Biosci, 48 (11–12), pp. 939–945 (1993) no month.

Wahl et al., Chemical Control of Bacterial Epibiosis on Ascidians, Marine Ecology Progress Series, vol. 110, pp. 45–57 (1994) no month.

Bobzin et al., Diterpenes From the Pohnepeian Marine Sponge Chelonaplysilla SP, Journal of Natural Products, vol. 54, No. 1, pp. 225–232, Jan.–Feb. (1991).

Uriz et al., Relationships of Biological and Taxonomic Characteristics to Chemically Mediated Bioactivity in Mediterranean Littoral Sponges, Marine Biology, 113, pp. 287–297 (1992) no month.

Minturn Wright, Antibiotic and Antifouling Properties of Marine Invertbrate Extracts: Comparative Aspects of Sponges and Gorgonians, Bioactivity Compounds From Marine Organism, Thompson et al. eds., pp. 351–356 (1991) no month.

D.J. Faulkner, Marine Natural Products, Natural Products Report, 4, pp. 539–576 (1986) no month.

Chang et al., Antibiotic Substances Produced by a Marine Green Alga, *Dunaliella promolecta*, Bioresource Technology, 44 (2) pp. 149–153 (1993) no month.

Coll et al., The Application of Vacuum Liquid Chromatography to the Separation of Terpene Mixtures, Journal of Natural Products, vol. 49, No. 5, pp. 934–936 (1986) no month.

Gerhart et al., Chemical Ecology and the Search for Marine Antifoulants, Journal of Chemical Ecology, vol. 14, No. 10, pp. 1905–1915 (1988) no month.

Glombitza et al., Antibiotics from Algae XXXIII[1]: Phlorotannins of the Brown Alga Minanthalia Elongaga [2,3], Planta Medica, 51, pp. 42–46 (1984) no month.

Matsunaga et al., Bioactive Marine Metabolites, VIII. Isolation of an Antimicrobial Blue Pigment from the Bryozoan Bugula Dentata, Experientia, 42, 84 (1986) no month.

Paul J. Scheuer, Some Marine Ecological Phenomena: Chemical Basis and Biomedical Potential, Sciences, 248, pp. 173–177 (1990) no month.

Sears et al., Antifouling Agents From Marine Sponge, Journal of Chemical Ecology, vol. 16, No. 3, pp. 791–799 (1990) no month.

(List continued on next page.)

*Primary Examiner*—Anthony Green
*Attorney, Agent, or Firm*—Dilworth & Barrese

[57] ABSTRACT

Aquatic organism repellent agents are derived from algae, sponges, tunicates, bryozoans, echinoderms and coelenterates and prevent the attachment and accumulation of microscopic and macroscopic organisms to surfaces in aquatic environments. One or more of the agents may be incorporated into a carrier for release of the agent in the locus to be protected.

24 Claims, No Drawings

OTHER PUBLICATIONS

Dilip de Silva et al., Manoalide, An Antibiotic Sesterterpenoid From the Marine Sponge *Luffariella variabilis* (Polejaeff), Tetrahedron Letters, vol. 21, pp. 1611–1614 (1980) no month.

Davis et al., Epibiosis of Marine Algae and Benthic Invertebrates: Natural Products Chemistry and Other Mechanims Inhibiting Settlement and Overgrowth, Bioorganic Marine Chemistry, Springer–Verlag Berlin, 3, pp. 85–114 (1987) no month.

Quinn Chemistry of Aqueous Marine Extracts: isolation techniques, Bioorganic Marine Chemistry, Scheuar eds., vol. 2 pp. 2–4 (1987) no month.

Lustigman et al., Antibiotic Production by Marine Algae Isolated from the New York/New Jersey Coast, Bull. Environ. Contam. Toxicol., 46, pp. 329–335 (1991) no month.

del Giorgio et al., Respiration Rates in Bacteria Exceed Phytoplankton Production in Unproductive Aquatic Systems, Nature, vol. 385, (1997) no month.

Caccamese et al., Antimicrobial and Antiviral Activities of Some Marine Algae from Eastern Sicily, Botanica Marina vol. XXIV, pp. 365–367 (1981) no month.

Capon et al., Antimicrobial Metabolites from a Pacific Sponge, Agelas sp., J. Am. Chem. Soc. 106, pp. 1819–1822 (1984) no month.

Amade et al., Antimicrobial Activities of Marine Sponges from the Mediterranean Sea, Marine Biology, pp. 271–275 (1987) no month.

Hornsey et al., The Production of Antimicrobial Compounds by British Marine Algae I, Brit. phycol. J. 9, pp. 353–361, (1974) no month.

Azumi et al., Inhibitory Effect of Halocyamine, an Antimicrobial Substance from Ascidian Hemocytes, on the Growth of Fish Viruses and Marine Bacteria, Experientia, 46, pp. 1066–1068 (1990) no month.

Burkholder, Antimicrobial Activity of Some Marine Sponges, Nature, vol. 222, pp. 983–984 (1969) no month.

Bergquist et al., The Incidence of Antibacterial Activity in Marine Demospongiae, Systematic and Geographic Considerations, Mar. Ecol. Prog. Ser., pp. 215–221 (1978) no month.

De Nys et al., Broad Spectrum Effects of Secondary Metabolites from the Red Alga *Delisea pulchra* in Antifouling Assays, Biofouling, vol. 8, pp. 259–171 (1995) no month.

Sreenivasa Rao et al., Antibacterial Activity of Indian Seaweed Extracts, Botanica Marina, Vo. XXIV, pp. 577–582, (1981) no month.

Pesando et al., Screening o Marine Algae from the French Mediterranean Coast for Antibacterial and Antifungal Activity, Botanica Marina, vol. XXVII, pp. 381–386 (1984) no month.

Nigrelli et al., Ectyonin, an Antimicrobial Agent from the Sponge, *Microciona prolifer*, Verrill, Zoologica, 44, pp. 173–177 (1959) no month.

Faulkner, interesting Aspects of Marine Natural Products Chemistry, Tretrahedron, vol. 33, pp. 1421–1443 (1977) no month.

Walls et al., Fouling, surface bacteria and antibacterial agents of four bryozoan species found in Tasmania, Australia, J. Exp. Mar. Biol. Ecol., 169, pp. 1–13 (1993).

Becerro et al., Antimicrobial Activity and Surface Bacterial Film in Marine Sponges, J. Exp. Mar. Biol. Ecol., 179, pp. 195–205 (1994).

Nakatsu et al., Biologically–Active Sterol Sulfates From the Marine Sponge *Toxadocia zumi*, Experientia, Birkhauser Verlag, CH–4010, 39, pp. 759–761 (1983) no month.

Hornsey et al., The Production of Antimicrobial Compounds by British Marine Algae II. Seasonal Variation in Production of Antibiotic, Br. Phycol. J. 11: 63 67, pp. 63–67, (1976) no month.

Targett et al., Antifouling Agents Against the Benthic Marine Diatom, J. of Chemical Ecology, vol. 9, No. 7, pp. 817–829 (1983) no month.

Bakus et al., The Use of Natural and Synthetic Toxins as Shark Repellents and Antifouling Agents, Toxicon, Suppl. 3, pp. 25–27 (1983) no month.

D. J. Faulkner, Antibiotics From Marine Organisms, Topics in Antibiotic Chemistry, vol. 2, Sammes, ed., pp. 13–58 (1978) no month.

D. J. Faulkner, Marine Natural Products, Natural Product Reports, vol. 3, pp. 1–33 (1986) no month.

D. J. Faulkner, Marine Natural Products: Metabolites of Marine Algae and Herbivorous Marine Molluscs, Natural Product Reports, vol. 1, pp. 251–280 (1984(a)) no month.

D. J. Faulkner, Marine Natural Products: Metabolites of Marine Invertebrates, Natural Product Reports, vol. 1, pp. 551–598 (1984(b)) no month.

D. J. Faulkner, Marine Natural Products, Natural Product Reports, vol. 5 (6), pp. 613–663 (1988).

D. J. Faulkner, Marine Natural Products, Natural Product Reports, vol. 7 (4), pp. 269–309 (1990).

D. J. Faulkner, Marine Natural Products, Natural Product Reports, vol. 8 (2), pp. 97–147 (1991).

Ohta, et al., Antibiotic Substance Produced by a Newly Isolated Marine Microalga, Chlorococcum HS–101, Bull. Environ. Contam. Toxicol., vol. 50 pp. 171–178 (1993) no month.

Targett, et al., Natural Antifoulants and Their Analogs: Applying Nature' Defense Strategies to Problems of Biofouling Control, Recent Developments in Biofouling Control, Thompson et al., eds., pp. 221–227 (1994) no month.

Chemical Abstract No. 70:80837 (Dec. 1968).
Chemical Abstract No. 99:102520 (1983) no month.
Chemical Abstract No. 102:91141 (1984) no month.
Chemical Abstract No. 104:83795 (Nov. 1985).
Chemical Abstract No. 111:235114 (1989) no month.
Chemical Abstract No. 114:182417 (1991) no month.
Chemical Abstract No. 119:98086 (Nov. 1993).
Chemical Abstract No. 120:49991 (1993) no month.
Chemical Abstract No. 123:108264 (1995) no month.
Chemical Abstract No. 123:281148 (1995) no month.

Rao et al., "Bioactivity in Marine Algae", Bioactive Compounds From Marine Organisms, Eds. M.F. Thompson, et al., 1991 Balkema/Rotterdam, pp. 374–377 no month.

A.B. Tadros, "The role of marine orgnanisms in fouling control", Pigment and Resin Technology, Jul. 1989, pp. 4–7 no month.

Bakus et al., "Toxins from Marine Organisms: Studies on Antifouling", Toxins, Drugs and Pollutants in Marine Animals, Bolus et al. eds., 1984, pp. 43–46 no month.

Nakatsu et al., "Biologically–active sterol sulfates from the marine sponge *Toxadocia zumi*", Experientia 39, 1983, Birkhäuser Verlag, CH–4010 Basel/Switzerland, pp. 759–761 no month.

Keifer et al., "Bioactive Bromopyrrole Metabolites from the Caribbean Sponge *Agelas conifera*", J. Org. Chem. 1991, 56, pp. 2965–2975 no month.

Sr. Alevin Mary, et al., "Bacterial–Barnacle Interaction: Potential of Using Juncellins and Antibiotics to Alter Structure of Bacterial Communities", Journal of Chemical Ecology, 19:10, 1993, pp. 2155–2167 no month.

Iorizzi, et al., "Chemical and Biological Investigation of the Polar Constituents of the Starfish *Luidia clathrata*, Collected in the Gulf of Mexico", Journal of Natural Products, 58:5, 653–671, May 1995.

R De Nys, et al., "Broad Spectrum Effects of Secondary Metabolites From The Red Alga *Delisea pulchra* in Antifouling Assays", Biofouling, 1995, 8, pp. 259–271 no month.

Marine Biology 88, 11–21 (1985) no month, Screening and bioassays for biologically–active substances from forty marine sponge species from San Diego, California, USA.

Marine Biology 89, 1–8 (1985) no month, Antimicrobial activity of tropical and subtropical sponges.

AQUATIC ANTIFOULING COMPOSITIONS AND METHODS

This is a continuation of application Ser. No. 08/164,328 filed on Dec. 9, 1993, now abandoned.

BACKGROUND OF THE INVENTION

1. Field of the Invention

This invention relates to prevention of fouling of surfaces in aquatic environments by microscopic and macroscopic organisms. More particularly, antifouling agents, compositions, coatings and methods for repelling and preventing attachment, growth and proliferation of biofouling organisms are disclosed.

2. Description of Related Art

Biofouling organisms settle on surfaces that are submerged in aquatic environments. Submerged surfaces such as water pipes, power plant water intake systems, sewer pipes, boat hulls, heat exchangers, grids, and the like are prone to biofouling. Biofouling is a major problem for most industries involved with fresh or salt water environments. Aquatic pests frequently clog pipes or become attached to submerged surfaces thus interfering with normal operations. For example, warm water associated with power plant cooling systems provides an ideal environment for the attachment and growth of aquatic organisms. Biofouling organisms also attach to other surfaces which contact aqueous solutions such as fishing nets, buoys, pilings, off-shore platforms, lumber, roofs, and concrete.

When a clean surface is introduced into an aquatic environment, it typically becomes coated with a conditioning layer of hydrophobic dissolved organic compounds. Microorganisms such as bacteria, algae, fungi, and protozoa attach to the conditioning layer and establish colonies which result in the formation of a slime layer. Such slimes can cause problems, e.g., by significantly reducing heat transfer across exchangers in cooling systems. Furthermore, slime layers contribute to the establishment of biofouling communities because planktonic (free floating) larvae of many invertebrate biofouling organisms are physically and chemically attracted to the slime layer. Examples of invertebrate bifouling organisms include mollusks such as mussels and oysters, and crustaceans such as barnacles. The release of specific compounds from the slime layer can also trigger metamorphosis of the planktonic larvae (see Hadfield (1986) Bull. Mas. Sci. 39:418–425 and Young and Mitchell, (1973) Int. Biodeterior. Bull. 9:105–109).

The blue mussel, *Mytilus edulis*, presents a particular problem at coastal power plants located in the Northeastern region of the United States. *Mytilus edulis* planktonic larvae settle on and attach to any available substratum. More recently, zebra mussels have begun to clog structures submerged in fresh water or brackish water environments. Settled juveniles grow rapidly and form dense aggregates which cause such problems as clogging inflow or outflow pipes.

Biofouling of underwater structures such as power plant water intake systems and heat exchangers results in significant economic losses to industry. Decreased fuel efficiency, increased cleaning and maintenance expenses, as well as outage expenses all contribute to increased economic expenditures. The incentive for preventing marine biofouling is great. As a result, various methods and compositions have been developed for prevention of marine biofouling. For example, utilities employ several methods for removing established biofouling communities. Periodic power outages are employed to physically enter power plant systems to remove organisms and debris. In addition, utilities often attempt to kill established biofouling communities by pumping large volumes of chlorine and molluscicides through water handling systems. However, these methods are slow acting and adversely affect the local ecology downstream from the effluent. Furthermore, these chemical treatments are inefficient because toxins are mixed in bulk water phase in an attempt to treat a surface phenomenon. Certain organisms such as the blue mussel can sense sub-lethal concentrations of some toxins and seal themselves off for long periods thereby effectively preventing contact with the toxins. Therefore, another drawback of certain existing chemical treatments is that relatively large toxic doses must be maintained for extended periods to effectively eliminate biofouling pests.

Ablative toxic antifouling coatings containing tributyl tin, copper alloys, mercury compounds, or cathodic protection have also been employed to control fouling. These antifouling coatings may include toxins which are leached into the aquatic environment to inhibit biofouling. The following examples of antifouling coatings are included for purposes of illustration. U.S. Pat. No. 5,096,488 describes a vinyl polymer or copolymer emulsion containing certain enumerated ammonium compounds. U.S. Pat. No. 5,116,407 describes an antifouling marine coating containing certain enumerated amine compounds acting as paint binders and marine biocides. U.S. Pat. No. 5,143,545 describes an antifouling marine paint containing certain enumerated water insoluble antibiotics said to be toxic to gram negative organisms of the genus Oceanospirillum, and a metallic compound, i.e., copper, tin, or zinc, acting as a marine biocide. U.S. Pat. No. 5,199,977 describes an antifouling paint containing a polymeric metal containing hybrid salt and certain enumerated organic ligands.

Observations have been made that certain sea creatures are associated with bioactive compounds. Attempts have been made to determine whether specific sponges are associated with compounds that have antimicrobial activity. Thompson et al., Marine Biology 88, 11–21 (1985), describe screening and bioassays for biologically active substances from sponge species near California, USA. Various extracts and metabolites are described as being biologically active but none of the substances was active in all assays.

A preemptive antifouling composition is needed for treating surfaces in aquatic environments which is highly effective and (1) does not contain heavy metals or synthetic toxins that adversely affect the local ecology, (2) is easy to manufacture and incorporate into or on undersea structures, (3) is easily cleaned and (4) has a prolonged effective lifetime. The benefits associated with such a composition would be enormous.

SUMMARY OF THE INVENTION

The present invention provides compounds and compositions which repel undesirable aquatic pests in an underwater environment. Aquatic organism repellents are derived from algae, tunicates, bryozoans, echinoderms and coelenterates. The present invention further provides antifouling compositions made of a carrier and an effective amount of an aquatic organism repellent derived from a creature selected from the group consisting of sponges, red algae, brown algae, green algae, tunicates, bryozoans, echinoderms and coelenterates. A method for reducing biofouling of a structure involves providing an antifouling composition as above and placing the antifouling composition in adherent contact with the structure. The present invention also provides a method of manufacturing an antifouling composition by obtaining at least one aquatic organism repellent extract from a creature selected from the group consisting of sponges, red algae, brown algae, green algae, tunicates, bryozoans, echinoderms and coelenterates, providing a carrier which is compatible with at least one of the repellents and combining the repellent extract with the carrier. The present invention further provides articles of manufacture which are resistant to biofouling which have a structure in adherent contact with an antifouling composition as described above.

DETAILED DESCRIPTION OF THE INVENTION

In one aspect, the present invention is directed to compounds and/or extracts of creatures that live in aquatic environments that repel, prevent or otherwise deter aquatic pests from settling on or near target locations. Bioactive repellent agents according to the present invention are relatively environmentally friendly because they are biodegradable and effective in low concentrations. The repellents are naturally occurring compounds derived or extracted from underwater creatures which are "distasteful" or even toxic to underwater pests. Certain of the repellent agents possess varying degrees of hydrophobicity. As will be seen below, the hydrophobic nature of the repellents provide several advantages. Repellents according to the present invention are potent, chemically stable, relatively insoluble in water, thermally stable, and are easily harvested.

Bioactive agents (toxicants or repellents) of the present invention are derived from algae, such as Rhodophyta (red algae), Chlorophyta (green algae), Phaeophyta (brown algae), Chrysophyta (golden algae) and microalgae, and other aquatic creatures such as tunicates, sponges, coelenterates, echinoderms and bryozoans. Such bioactive agents repel or are toxic to microorganisms such as bacteria, yeast, and diatoms. The repellents are also effective against macroorganisms such as mollusks and crustaceans.

Polar or semi-polar solvents are used as the vehicles for obtaining active repellents from the above-identified creatures. The creatures are collected and then soaked in and/or blended with the solvent. Alternatively, the creatures can be homogenized in a blender in distilled water, optionally lyophilized, and then mixed with the solvent to provide an extract. Any non-polar or semi-polar solvent is suitable as long as it does not adversely react with the active repellent constituent(s) to reduce activity. Suitable solvents include ethanol, methanol, ethyl acetate, hexane, chloroform, acetonitrile and dimethylformamide.

In one embodiment, suitable creatures according to the present invention, e.g., green algae, are collected, gently cleansed, and frozen until ready for further processing. The algae is then blender homogenized in distilled water (about 1:3 weight/volume). The resulting homogenate is then lyophilized, resuspended in hexane and sonicated for about 30 minutes. The resulting mixture is then centrifuged resulting in a supernatant and a pellet. The solvent is then removed from the supernatant using a vortex vacuum evaporator. The pellet is then extracted with ethyl acetate and centrifuged. The resulting supernatant is separated from the resulting pellet. The solvent is removed from the supernatant using a vortex vacuum evaporator. The pellet is further extracted with methanol and centrifuged. Solvent is removed from the resulting supernatant using a vortex vacuum evaporator. Each extract is then tested for repellent activity as described below.

In an alternative embodiment, the collected, cleansed creatures are blended and extracted overnight by immersion in solvent, e.g., methanol (about 250 gm:200 ml) in a beaker which is shaken at about 200 rpm on a rotary shaker table. After extraction, the liquid is removed and centrifuged and the supernatant is vacuum dried to obtain a solvent extract concentrate. Tissues remaining in the beaker are air dried, e.g., in a hood, and subjected to further solvent extraction, e.g., ethyl acetate and hexane extraction by repeating the procedures of this embodiment. Each extract is then tested for repellent activity as described below.

Repellent activity is assessed by assaying for bacterial inhibition activity, mussel byssal attachment activity, bacterial anti-settlement activity, and larvae anti-settlement activity.

To perform the bacterial inhibition assay each dried extract was dissolved in about 2 ml of original solvent to get a saturated solution. About twenty to fifty (20–50) μl of each solution was added to a sterile bio-assay disc (6 mm Difco™ 1599-33) and air dried. Three discs with extract and two control discs with only solvent (all vacuum dried) were placed on a semi-solid (half usual concentration) tryptic soy agar (TSA) plate inoculated with a dilute microbial suspension. The plates were incubated for about 24 hours at room temperature. Five bacterial (*Vibrio sp., Escherichia coli, Serratia marinarubra, Bacillus subtills* and *Pseudomonas aeruginosa*) and a yeast (*Candida albicans*) were used in the antibiotic assay for each extract. The halo around the dics was measured and the assay was scored: highly positive (+++) if D (a zone of inhibition) was greater than 2 mm, positive (++) if D was between 1.0–2.0 mm, weakly positive if D was between 0.5–1.0 mm and no positive activity (−) if D<0.5 min. The bacterial inhibition assay was performed on green algae, brown algae, compound ascidian, red algae, boring sponges, bryozoans and sea stars. The results are depicted in Table 1. According to K. L. Gosner, Peterson Field Guide to Atlantic Seashore, (1978) pg. 36, *F. evanescens, F. edentatus*, and *F. filiformis*, may be indistinguishable from variant *vesiculosus* and bladderless *spiralis* unless "in fruit." Indeed, these 3 species are regarded by some botanists as merely ecological variants of *F. distichus*.

EXAMPLES 1–16

TABLE 1

Bacterial Growth Inhibition Activity

| | | | Anti-bacterial activity# | | | | | |
|---|---|---|---|---|---|---|---|---|
| Organism | Latin name | Solvent* | Vibrio sp. | E. coli | S. mari | C. alb | P. aerug. | B. subtilis |
| 1 Green algae | Ulva sp. | E.A. | +++ | − | ++ | − | − | ++ |
| 2 Green algae | Ulva sp. | Met | +++ | − | ++ | − | − | ++ |

TABLE 1-continued

Bacterial Growth Inhibition Activity

| | | | Anti-bacterial activity# | | | | | |
|---|---|---|---|---|---|---|---|---|
| Organism | Latin name | Solvent* | Vibrio sp. | E. coli | S. mari | C. alb | P. aerug. | B. subtilis |
| 3 Brown algae | Fucus evanescens | E.A. | ++ | − | − | − | − | − |
| 4 Brown algae | Fucus evanescens | Met | +++ | − | − | − | − | +++ |
| 5 Brown algae | Fucus evanescens | Water | +++ | − | − | − | − | +++ |
| 6 Brown algae | Ascophyllum sp. | Met | +++ | − | − | − | − | ++ |
| 7 Brown algae | Ascophyllum sp. | Water | +++ | − | − | − | − | +++ |
| 8 Compound ascidian | Didemnum sp. | Hex | − | − | − | − | − | + |
| 9 Compound ascidian | Didemnum sp. | E.A. | − | − | − | − | − | +++ |
| 10 Compound ascidian | Didemnum sp. | Met | − | − | − | − | − | +++ |
| 11 Red algae | Chondrus sp. | Hex | +++ | − | − | − | − | + |
| 12 Boring (yellow) sponge | Cliona sp. | E.A. | ++ | − | − | − | − | ++ |
| 13 Bryozoan | Bugula sp. | E.A. | − | − | − | − | − | ++ |
| 14 Sea star | Asterias sp. | E.A. | + | − | − | − | − | − |
| 15 Sea star | Asterias sp. | Met | + | − | − | − | − | + |
| 16 Green algae | Codium sp. | E.A. | + | − | − | − | − | − |

*Met: methanol, E.A.: ethyl acetate, Hex: hexane
Highly positive (+++):D > 2 mm
Positive (++):1 < D < 2
Weakly positive(+):0.5 < D < 1
Negative (−):D < 0.5 mm To perform the mussel byssal thread attachment assay, juvenile blue mussels, *Mytilus edulis*, were collected from tidal rocks and maintained in an aquarium with seawater at 18° C. on a diet of the microalga, *Isochrysis galbana* (a haptophyte) until needed. Frosted slides (3×1') were washed with methanol and dried before use. The sample zone was coated with a test extract which was re-dissolved in its solvent as above. After the solvent was completely evaporated, two juvenile mussels (about 1-2 cm in shell length) were fixed around the edge of the sample zone using a commercial super glue (Duro™). The bioassay slides prepared in this way were placed at the bottom of an aquarium with running sea water. The turnover time of the seawater was set to be about 1 hour for the first 12 hours to minimize the contamination of seawater by the extract. The mussels tried to attach themselves on the slide using many byssal threads. If an extract was bioactive, most byssal threads secreted by mussels avoided the sample zone. The mussel byssal thread inhibition assay was performed on green algae, brown algae, ascidian, compound aseidian, red sponge, bryozoans and sea stars. The result of the assay are depicted in Table 2.

EXAMPLES 17-31

TABLE 2

Mussel Byssal Thread Inhibition Activity

| Organism | Latin name | Solvent* | Mussel thread inhibition |
|---|---|---|---|
| 17 Green algae | Ulva sp. | E.A. | H |
| 18 Green algae | Ulva sp. | Met | H |
| 19 Brown algae | Fucus evanescens | E.A. | P |
| 20 Brown algae | Fucus evanescens | Met | P |
| 21 Brown algae | Ascophyllum sp. | Met | P |
| 22 Ascidian | Didemnum sp. | E.A. | P |
| 23 Compound ascidian | — | E.A. | H |
| 24 Red sponge | Microciona sp. | E.A. | P |
| 25 Red sponge | Microciona sp. | Met | P |
| 26 Boring (yellow) sponge | Cliona sp. | E.A. | P |
| 27 Boring (yellow) sponge | Cliona sp. | Met | P |

TABLE 2-continued

Mussel Byssal Thread Inhibition Activity

| Organism | Latin name | Solvent* | Mussel thread inhibition |
|---|---|---|---|
| 28 Bryozoan | Bugula sp. | E.A. | P |
| 29 Sea star | Asterias sp. | E.A. | P |
| 30 Green algae | Codium sp. | E.A. | P |
| 31 Green algae | Codium sp. | Met | H |

*Met: methanol, E.A.: ethyl acetate, Hex: hexane
Highly positive inhibition (H)
Positive inhibition (P)

To perform the bacterial anti-settlement assay, a total of about 0.5 ml extract was spread onto the frosted portion of six glass slides and the solvent was evaporated. An equal number of control slides was treated with pure solvent in an identical manner. Each slide was placed into a 50 ml Falcon tube filled with approximately $10^6$ cells $ml^{-1}$ of *Pseudomonas aeruginosa*. Log-phase cells were used because growth status of the bacterial can affect their attachment significantly. The tubes were capped and placed horizontally onto a rotary shaker so that the treated surfaces faced downward.

Tubes were removed randomly from the tray at time intervals of about 1-2 hours. Slides were slowly immersed in about 2% formaldehyde to remove excess water as well as fixing the bacteria. About thirty microliters of a fluorescent stain (DAPI) was added, the cover slip dropped and the number of attached bacteria counted in 20 fields on an epifluorescent microscope. The bacterial anti-settlement assay was performed on green algae, brown algae, ascidian, red algae and bryozoans. The results of the assay are depicted in Table 3.

EXAMPLES 32–38

TABLE 3

Bacterial Anti-Settling Activity

| | | | Bassel anti-settling activity # | |
|---|---|---|---|---|
| Organism | Latin name | Solvent* | *P. aeruginosa* | *E. coli* |
| 32 Green algae | Ulva sp | E.A. | H | — |
| 33 Brown algae | Fucus evanescens | E.A | H | H |
| 34 Brown algae | Fucus evanescens | Met | H | — |
| 35 Brown algae | Ascophyllum sp. | Met | H | H |
| 36 Ascidian | Didemnum sp. | Met | P | — |
| 37 Red algae | Chondrus sp. | Hex | P | — |
| 38 Bryozoan | Bugula sp. | Met | — | H |

*Met: methanol, E.A.: ethyl acetate, Hex: hexane
Highly positive inhibition (H)
Positive inhibition (P)

To perform the coated slide larval anti-settlement assay, pre-setting mussel and oyster larvae with shell length of about 250–300 μm were used and stored at 8° C. The tested extract was coated on frosted glass and air dried. Coated and clean (control) slides were placed in an aquarium with flowing seawater. The turnover time of the seawater is set to be about 1 hour for the first 12 hours to minimize the contamination due to the extract. *I. galbana* diet is added into the aquarium with flowing seawater. Larval density was 2 larvae $ml^{-1}$. The container was aerated with two air stones. Tested slides and control slides were removed and the number of larvae settled on them was calculated and compared. The larval anti-settlement assay was performed on green algae, boring sponges and brown algae. The results of the assay are depicted in Table 4.

EXAMPLES 39–41

TABLE 4

Mussel and Oyster Larval Settlement Inhibition

| Organism | Latin name | Solvent* | Larval settlement inhibition |
|---|---|---|---|
| 39 Green algae | Codium sp. | E.A. | P |
| 40 Boring (yellow) sponges | Cliona sp. | Met | P |
| 41 Brown algae | Fucus evanescens | Met | P |

*Met: methanol, E.A.: ethyl acetate, Hex: hexane
Positive inhibition (P)

According to the present invention, the aquatic pest repellents are incorporated into an acceptable carrier or vehicle to deliver repellent activity to desired target sites. The hydrophobic nature of the active constituents is advantageous in certain instances because such constituents are not freely dissolved and/or diluted in aqueous environments and are thus adapted to be maintained at the desired location by various immobilization techniques.

Thus, in another aspect, the present invention provides compositions which reduce or completely eliminate fouling of underwater structures by aquatic pests. The compositions include a carrier which contains at least one of the above-described antifouling agents that repel, prevent or otherwise deter aquatic pests from settling on structures incorporating the compositions. In accordance with one aspect of the present invention, the unique combination of carrier and antifouling agent augment one another by creating a slippery surface which causes problems for organisms attempting to anchor on the surface and, further, a chemically hostile local environment that the organisms find "distasteful" and in some cases toxic. Antifouling agents or repellents according to the present invention are bioactive compounds derived from natural sources that upon entry into the ecosystem are biodegradable and environmentally friendly.

Repellents according to the present invention can be incorporated into structural members to provide aquatic pest repellent structures which are intended to be placed in aquatic environments. In this manner, the structure itself has integral aquatic pest repellency. The inventive antifouling agents can also be incorporated into surface coatings of structures intended for underwater use. Materials which can incorporate the antifouling agents are known and must be compatible with the repellents, i.e., there is no interaction between the materials and the repellents which degrades or is otherwise detrimental to the repellent activity of the antifouling agents.

Vehicles (a structure or coating) which contain one or more repellent agents provide a medium which allow the bioactive compounds to exert repellent activity in the locus to be protected over a period of time either by sustained release of the agent(s) or by creating a fixed effective surface concentration of the agent.

Diffusional systems are well suited to release the repellent agents to target areas. Diffusional systems include reservoir devices in which a core of repellent is surrounded by a porous membrane or layer, or matrix devices in which the repellent is distributed throughout an inert matrix. Materials which may be used to form reservoirs or matrices include silicones, methacrylates, vinyl compounds such as polyvinyl chloride, olefins such as polyethylene or polypropylene, fluoropolymers such as polytetrafluoroethylene and polyesters such as terephthalates. The diffusional systems may be molded into a film or other layer material which is then placed in adherent contact with the structure intended for underwater use. Alternatively, the repellent agent may be mixed with a resin, e.g., polyvinyl chloride and then molded into a desired shape, e.g., a pipe, which integrally incorporates the repellent to form a structure having inherent fixed repellency. Increasing the concentration of fixed repellent at or near the surface allows increased efficacy. Alternatively, the entire structural member may be a porous matrix which allows diffusion of the repellent into the surrounding environment.

Repellents according to the present invention may be applied as surface coatings which are corrosion resistant and applied by painting or otherwise bonding or adhering a liquid or paste-like composition containing the repellent to the material intended for underwater use. After applying the liquid or paste coating, it hardens to form a repellent coating. The coatings may be applied in a variety of ways which are known in the art. Mastic coatings, polymerizable compositions, or solvent based paints which contain one or more repellents can be applied to structures intended for underwater use.

Materials which may be used as coating vehicles include phenolic resins, silicone polymers, chlorinated rubbers, coal tar and epoxy combinations, epoxy resin cured from a solvent solution with polyfunctional amines, polyamide resins, vinyl resins in solvent solutions, elastomers, fluoropolymers, polyesters and polyurethanes. Especially preferred vehicles for the repellent agents of the present invention are silicone polymers. Silicone resins, silicone RTV polymers, and silicone heat cured rubbers are suitable and are described in the Encyclopedia of Polymer Science and Engineering, Vol. 15, pp. 204 et seq. (1989) hereby incorporated by reference. Polydimethyl siloxanes are very well suited as a vehicle for containing the inventive repellents. These compositions create a slippery surface that, as was discussed above, augments the chemical repellent activity of the repellent agents.

Microencapsulation techniques are useful in maintaining sustained focal release of repellents according to the present invention. Microencapsulation may also be used for providing improved stability of the antifouling composition. The active agents of the present invention may be microencapsulated in structures in the form of spheres, aggregates of core material embedded in a continuum of wall material, capillary designs or incorporated into films and paints. The core material of a microcapsule containing a repellent agent may be in the form of a liquid droplet, an emulsion, a suspension of solids, a solid particle, or a crystal. The microcapsule coating material may be an organic polymer, hydrocolloid, wax, fat, lipid, metal, or inorganic oxide. Silicone polymers are the most preferred microcapsule coating material for use with the present invention. Microencapsulation techniques are well known in the art and are described in the Encyclopedia of Polymer Science and Engineering, Vol. 9, pp. 724 et seq. (1989) hereby incorporated by reference.

The bioactive repellent in association with an acceptable carrier may be applied to submersible or submerged surfaces such as water intake systems, water cooling tubes, heat exchangers, and any other surfaces which are subject to biofouling. For example, the composition may be employed as an antifouling composition for boat hulls, fishing netting, buoys, pilings, lumber, roofs, and concrete. Dipping, spraying, brushing and laminating are other means for applying the antifouling composition. Furthermore, the novel antifouling composition may be used for removing microorganisms from surfaces in hospitals or other surfaces where an aseptic environment is desirable.

The examples and embodiments depicted in this specification are not intended to be limitations on the inventive concept described herein. Accordingly, one with skill in the art may make modifications in the methods and products which are intended to be covered by the following claims.

What is claimed is:

1. An antifouling composition comprising a carrier suitable for underwater application and an effective antifouling amount of at least one aquatic organism repellent derived from a creature selected from the group consisting of *Microciona sp., Cliona sp., Fucus evanescens, Ascophyllum sp., Chondrus sp., Asterias sp.* and *Codium sp.*, the carrier being compatible with the repellent.

2. An antifouling composition according to claim 1, wherein said carrier comprises a polymer which is compatible with said repellent.

3. An antifouling composition according to claim 2, wherein said polymer comprises a water insoluble polymer.

4. An antifouling composition according to claim 3, wherein said water insoluble polymer is a homopolymer or copolymer derived from a material selected from the group consisting of silicone polymers, vinyl polymers, epoxys, olefins, polyesters, polyamides and fluoropolymers.

5. An antifouling composition according to claim 4, wherein said polymer is selected from the group consisting of polydimethyl siloxane, polyethylene, polypropylene, polyvinyl chloride, polyethylene terephthalate, polyurethane and polytetrafluoroethylene.

6. An antifouling composition according to claim 1, wherein said repellent is an antibiotic.

7. An antifouling composition according to claim 1, wherein said repellent is effective against an organism selected from the group consisting of bacteria, yeast, fungi and diatoms.

8. An antifouling composition according to claim 1, wherein said repellent is effective against an organism selected from the group consisting of mollusks and crustaceans.

9. An antifouling composition according to claim 1, wherein said carrier comprises a film, reservoir, matrix or paint.

10. A method of reducing fouling of a structure comprising providing an antifouling composition which comprises a carrier suitable for underwater application and an effective antifouling amount of at least one aquatic organism repellent derived from a creature selected from the group consisting of *Microciona sp., Cliona sp., Fucus evanescens, Ascophyllum sp., Chondrus sp., Asterias sp.* and *Codium sp.*, the carrier being compatible with the repellent; and placing said antifouling composition in adherent contact with the structure.

11. A method according to claim 10, wherein said carrier comprises a polymer which is compatible with said repellent.

12. A method according to claim 10, wherein said repellent is effective against an organism selected from the group consisting of bacteria, yeast, fungi and diatoms.

13. A method according to claim 10, wherein said repellent is effective against an organism selected from the group consisting of mollusks and crustaceans.

14. A method of manufacturing an antifouling composition comprising:

obtaining at least one aquatic organism repellent from a creature selected from the group consisting of *Microciona sp., Cliona sp., Fucus evanescens, Ascophyllum sp., Chondrus sp., Asterias sp.* and *Codium sp.*;

providing a carrier suitable for underwater application which is compatible with said repellent; and combining said repellent with said carrier to form an antifouling composition.

15. A method according to claim 14, wherein said carrier comprises a polymer which is compatible with said repellent.

16. A method according to claim 14, wherein said repellent is effective against an organism selected from the group consisting of bacteria, yeast, fungi and diatoms.

17. A method according to claim 14, wherein said repellent is effective against an organism selected from the group consisting of mollusks and crustaceans.

18. An article of manufacture which is resistant to biofouling comprising an aquatic structure incorporating an antifouling composition which comprises a carrier suitable for underwater application and an effective antifouling amount of at least one aquatic organism repellent derived from a creature selected from the group consisting of *Microciona sp., Cliona sp., Fucus evanescens, Ascophyllum sp., Chondrus sp., Asterias sp.* and *Codium sp.*, the carrier being compatible with the repellent.

19. An aquatic organism repellent comprising an extract derived from a creature selected from the group consisting of *Fucus evanescens, Ascophyllum sp., Chondrus sp., Asterias sp., Codium sp., Microciona sp.* and *Cliona sp.*

20. An aquatic organism repellant comprising an extract of *Ulva sp.* derived with a solvent selected from the group consisting of ethanol, methanol, ethyl acetate, hexane, chloroform, acetonitrile and dimethylformamide.

21. An aquatic organism repellent according to claim 20 wherein the repellant further comprises a carrier.

22. An aquatic organism repellent according to claim 21 wherein the carrier comprises a polymer.

23. An aquatic organism repellent according to claim 21 wherein the carrier comprises a film, reservoir, matrix or paint.

24. An aquatic organism repellent according to claim 20 wherein the extract is an antibiotic.

* * * * *